United States Patent [19]

Muzyczko et al.

[11] 3,994,826

[45] Nov. 30, 1976

[54] METHOD OF EMULSIFICATION

[75] Inventors: Thaddeus M. Muzyczko, Downers Grove; Jon A. Loboda, Chicago, both of Ill.

[73] Assignee: The Richardson Company, Des Plaines, Ill.

[22] Filed: Nov. 27, 1974

[21] Appl. No.: 527,775

Related U.S. Application Data

[63] Continuation-in-part of Ser. No. 865,519, Oct. 10, 1969, abandoned.

[52] U.S. Cl. .............................. 252/312; 252/314; 252/356; 252/8.5 P
[51] Int. Cl.$^2$ .......................................... B01J 13/00
[58] Field of Search ................ 252/356, 355, 312; 260/501.17, 501.19, 501.2

[56] References Cited
UNITED STATES PATENTS

| | | | |
|---|---|---|---|
| 1,970,578 | 8/1934 | Schoeller et al. | 252/356 X |
| 2,033,092 | 3/1936 | Bruson | 260/130 |
| 2,213,477 | 9/1940 | Steindorff et al. | 252/351 X |

Primary Examiner—Benjamin R. Padgett
Assistant Examiner—E. Suzanne Parr
Attorney, Agent, or Firm—Alan M. Abrams

[57] ABSTRACT

A method of emulsification comprising of utilizing salts of water-soluble organic acids and phenols with at least one salt-forming aminoalkylene group. An illustrative salt which can be used is the reaction product of dodecylbenzene sulfonic acid and 2,6-Bis(dimethylaminomethylene)-4-methyl phenol. These salts in combination with non-ionic surfactants provide particularly useful emulsifying systems in salt water, hard water and bacteria-containing systems.

9 Claims, No Drawings

METHOD OF EMULSIFICATION

CROSS REFERENCE TO RELATED APPLICATIONS

This application is a continuation-in-part application of our copending application Ser. No. 865,519 filed Oct. 10, 1969, now abandoned.

BACKGROUND OF THE INVENTION

1. Field of the Art

This invention relates to the method of using salts of water-soluble organic acids and certain aminoalkylene phenols as emulsifiers in water-oil systems.

2. Description of the Prior Art

Oil-in-water emulsions are important for many commercial products in cosmetics, agricultural pesticidical fluids, hydraulic fluids, oil well fluids and the like. In many instances, these products are used in association with salt water, hard water or bacteria-containing systems.

Many emulsification methods have been proposed, especially those incorporating the salts of amine substituted phenolic bases. However, as illustrated in the examples presented herein certain salts of amine substituted phenolic bases possess superior emulsification properties. Most notably are those which are the salts of a water-soluble organic acid and the phenol as illustrated below:

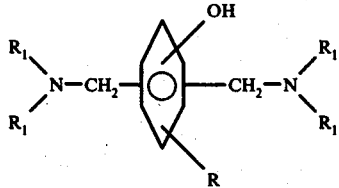

wherein R is alkyl having from 1 to 3 carbon atoms and $R_1$ is also alkyl having from 1 to 9 carbon atoms.

SUMMARY OF THE INVENTION

Briefly, our invention is directed to a method of emulsification using an emulsifier agent based on salts of organic acids and phenols wherein the phenol has at least one salt-forming aminoalkylene group. These salts are useful alone and in combination with non-ionic surfactants in forming emulsions.

In a broad embodiment our invention relates to a method for emulsifying oil-water systems which comprises adding an effective amount of an emulsifier agent comprising a salt of a water-soluble organic acid and a phenol having the following general formula:

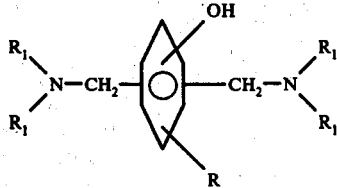

wherein R is alkyl having from 1 to 3 carbon atoms and $R_1$ is an alkyl having from 1 to 9 carbon atoms, to said system and forming an emulsion.

DETAILED DESCRIPTION OF THE INVENTION

The emulsifier salts of the invention are formed from water-soluble organic acids which provide a hydrocarbon functionality to aid in oil compatibility and advantageously are themselves anionic surface active agents in the salt form. Illustrative organic acids include water-soluble carboxylic, sulfonic, sulfuric, phosphoric and phosphonic acids with aliphatic, aromatic or naphthenic groups or their combination. Generally, they have about 2 to 30 carbon atoms in their organic portion and one or more acidic groups as in citric acid and are water-soluble. Suitable acids include ethanoic, butanoic, butanedioic, naphthyl butanoic, chlorobutanoic, hexanoic, dodecanoic, octadecanoic, octanedioic, octadecenoic, octadienoic, benzoic, methyl benzoic, hydroxy benzoic, methoxy benzoic, benzene dicarboxylic, biphenyl di-carboxylic, cyclohexane carboxylic acid and the like and corresponding forms of sulfonic, sulfuric, phosphoric and phosphonic acids particularly dodecyl sulfonic, octadecyl sulfonic, benzene sulfonic, methyl benzene sulfonic, dodecylbenzene sulfonic, octadecyl benzene sulfonic, hexyl sulfuric, octadecyl sulfuric, dodecyl phosphoric, methyl phosphonic, and the like.

Advantageously, the water-soluble organic acid is a carboxylic or sulfonic acid and more particularly an alkyl carboxylic, aryl carboxylic, alkaryl carboxylic, aralkyl carboxylic, alkyl sulfonic, aryl sulfonic, alkaryl sulfonic, or aralkyl sulfonic acid. Preferred are those with about 6–24 carbon atoms.

These acids are combined with phenols having two salt-forming aminoalkylene groups to form the desired emulsifiers. These phenols advantageously have the formula:

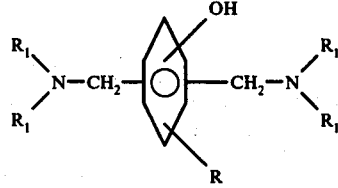

wherein R is alkyl having from 1 to 3 carbon atoms, and $R_1$ is alkyl having from 1 to 9 carbon atoms. $R_1$ may be identical or each can be of a different chain length. To possess desirable emulsification properties R is from only 1 to 3 carbon atoms as will be illustrated below.

These compositions are prepared advantageously through a Mannich reaction with phenols, alkyl phenols, or alkaryl phenols; aldehydes; and secondary amines; or through the use of sodium dialkylamines with di-chloromethyl-phenols.

The salts of the invention are formed by combining the defined water-soluble organic acids and phenols with one or more salt-forming aminoalkylene groups. When the phenol is a mixture of mono- and di-aminoalkylene phenols, usually a mixture of salts results. Advantageously, the salts are essentially neutralized as indicated by a pH of 5.0–7.0.

These salts are useful as emulsifiers alone and particularly in combination with non-ionic emulsifiers to form emulsifier concentrates containing from about 1–99 advantageously about 10–70, and preferably about 30–60 weight percent of the defined emulsifier salt. Suitable non-ionics are the types previously used in emulsifier mixtures of the prior art, in which the hydrophilic and lipophilic groups are so balanced as to aid in water dispersibility and advantageously water solubility. Typical non-ionics are adducts or derivatives of a polyoxyalkylene glycol or polyoxyalkylene phenol as known in this art. Illustrative non-ionics are described in U.S. Pat. No. 2,898,267.

The emulsifier salt of the invention or emulsifier concentrate is usually added to an oil such as kerosene, fuel oil, diesel oil, fatty oil or other light oil. Usually, the emulsifier component is present in about 0.5–50 weight percent and advantageously about 5–25 weight percent of the product with more specific ranges dependent on whether the product is to serve in a concentrated form or be emulsified directly without further oil addition.

The oil with emulsifier is then mixed with sufficient water to form the desired emulsion, which advantageously is an oil in water emulsion. Usually, about 20–98 weight of the resulting emulsion is water with a more frequent range being about 50–95 weight percent.

Other components are often present in these emulsions such as toxicants, perfumes and the like. These are commonly added to the oil-emulsifier composition before the emulsion is prepared.

With the use of the above defined emulsifier salt, emulsions are conveniently formed in salt water, hard water, bacteria-containing systems and other aqueous media.

The following examples illustrate some of the embodiments of this invention. It is to be understood that these are for illustrative purposes only and do not purport to be wholly definitive to conditions or scope.

EXAMPLES I – IV

Salts of toluene sulfonic acid, dodecylbenzene sulfonic acid, and laurylalcohol phosphate with 2,6-Bis(-diaminomethylene)-4-nonylphenol or a mixture of the mono- and di-aminomethylene substituted phenol were prepared and tested for emulsifying properties with kerosene and tap water. The kerosene contained chlordane as a typical toxicant in an amount of about 46 parts by weight per 39 parts by weight of kerosene.

Each salt was combined with an ethoxylated octylphenol in amounts shown in Table II below. This concentrate (about 20 parts by weight) was combined with the kerosene solution (about 80 parts by weight) and the emulsion was prepared by adding this concentrate (about 10 parts by weight) to tap water (about 50 parts by weight).

TABLE I

| Example | Acid | Amine | pH |
|---|---|---|---|
| I | Dodecylbenzene Sulfonic Acid | Mixture of mono- and di-amino methylated-4-nonyl-phenol | 5.0 |
| II | '' | Diaminomethylated-4-methyl phenol | 6.0 |
| III | '' | Diaminomethylated-4-nonylphenol | 5.0 |
| IV | Laurylalcohol Acid Phosphate | Above mixture | 6.5 |

TABLE II

| Example | Salt/Non-Ionic (Weight) | Stability of Emulsion |
|---|---|---|
| I | 30/70 | Spontaneous emulsion stable over 7 hours |
| II | 50/50 | Spontaneous emulsion stable beyond 48 hours |
| III | 40/60 | Spontaneous emulsion creamed after 4 hours |
| IV | 50/50 | Spontaneous emulsion creamed after 2 hours |

As can be observed from the results above, Example II was the best emulsifier in terms of maintaining the stability of an emulsion. This illustrates the properties associated with a particular emulsifier used according to the present claims.

EXAMPLE V

A salt of dodecylbenzene sulfonic acid (40 gm.) and a mixture (15 gm.) of mono- and di-aminomethylated nonylphenol was used in combination with ethoxylated octylphenol (50 gm.) to prepare an emulsion with soybean oil. The salt was at a pH of about 6.6. About 15 gm. of isopropanol was also present in the emulsifier mixture.

About 5 ml. of this mixture, 10 ml. of soybean oil, and 25 ml. of tap water were used to form an emulsion. A small amount of oil-degrading bacteria was added and the emulsion was found to be stable over 3 hours.

We claim as our invention:

1. A method of forming an oil-in-water emulsion system, comprising the steps of: adding an emulsifier agent to an oil, said emulsifier agent being added in an amount of from 0.5 to 50 percent, by weight, based on the combined weight of said oil and emulsifier agent, said emulsifier agent including a salt of a water-soluble organic acid and a phenol having the following general formula:

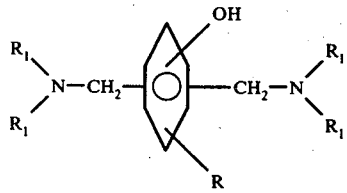

wherein R is alkyl having 1 to 3 carbon atoms and $R_1$ is alkyl having from 1 to 9 carbon atoms; combining said oil and emulsifier agent with water to form an oil-water system; and, agitating said system to an extent sufficient to effect the formation of an oil-in-water emulsion therein.

2. The method of claim 1 wherein said emulsifier agent is added in an amount of from 5 to 25 percent, by weight, based on the combined weight of said oil and emulsifier agent.

3. The method of claim 1 wherein each $R_1$ is methyl.

4. The method of claim 1 wherein the water-soluble organic acid is selected from the group consisting of alkyl carboxylic acid, aryl carboxylic acid, alkaryl carboxylic acid, aralkyl carboxylic acid, aryl sulfonic acid, alkyl sulfonic acid, alkaryl sulfonic acid, aralkyl sulfonic acid.

5. The method of claim 1 in that said acid is dodecylbenzene sulfonic acid.

6. The method of claim 1 in that said acid is dodecylbenzene sulfonic acid, and $R_1$ and R are methyl.

7. The method of claim 1 in that said emulsifier agent contains a non-ionic emulsifier selected from the group consisting of polyoxyalkylene glycol or polyoxyalkylene phenol, the amount of said salt to nonionic emulsifier ranges from 99:1 to 1:99 percent, by weight, based on the combined weights of said salt and nonionic emulsifier.

8. The method of claim 7 in that said emulsifier agent comprises from about 10 to about 70 weight percent of said salt.

9. The method of claim 8 in that said percent is from about 30 to about 60.

\* \* \* \* \*